United States Patent
Wharton

(10) Patent No.: US 6,194,455 B1
(45) Date of Patent: *Feb. 27, 2001

(54) TOPICAL MEDICAMENT FOR TREATING SKIN ULCERS

(76) Inventor: Marie Madeline Wharton, 3109 St. Claude Ave., New Orleans, LA (US) 61554

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/321,946

(22) Filed: May 28, 1999

(51) Int. Cl.[7] ............... A61K 31/235; A61K 31/715
(52) U.S. Cl. ............... 514/532; 514/53; 514/546; 514/882
(58) Field of Search ............... 514/532, 546, 514/53, 882, 12, 900; 424/422, 401

(56) References Cited

U.S. PATENT DOCUMENTS

| | | | |
|---|---|---|---|
| 4,945,084 | * | 7/1990 | Packman ............... 514/53 |
| 5,102,870 | * | 4/1992 | Florine et al. ............... 514/12 |
| 5,196,405 | * | 3/1993 | Packman ............... 514/53 |
| 5,246,697 | | 9/1993 | Conte et al. . |
| 5,411,738 | | 5/1995 | Hind . |
| 5,457,128 | * | 10/1995 | Yanaqawa ............... 514/532 |
| 5,478,814 | | 12/1995 | Packman . |
| 5,707,653 | | 1/1998 | Goldberg . |
| 5,709,873 | * | 1/1998 | Bar-Shalom et al. ............... 424/422 |
| 5,714,165 | | 2/1998 | Repka et al. . |
| 5,977,087 | * | 11/1999 | Pehrson, Sr. et al. ............... 514/53 |

FOREIGN PATENT DOCUMENTS

89/00047 * 1/1989 (WO) .

OTHER PUBLICATIONS

Meredith et al., Sucralfate for radiation mucocitis . . . , Int. J. Radiat. Oncol., Phys. vol. 37/2, pp. 275–279, (1997).*
Nguyen et al., Muciadhesive semisolid . . . , Eur. J. Biopharm. vol. 42/2, pp. 133–137, (1996).*
Hondalus et al., *Septicemic salmonellosis* . . . , J. of The American Vet.Med. Assoc. vol. 1192/4, pp. 527–529, (1988).*

* cited by examiner

*Primary Examiner*—Marianne M. Cintins
*Assistant Examiner*—Vickie Kim
(74) *Attorney, Agent, or Firm*—Michael I. Kroll

(57) ABSTRACT

A composition and method of treating skin ulcers utilizes a combination of sucralfate and a topical anesthetic such as lidocaine. The composition finds utility in treating the symptoms of d from herpes, acne, psoriasis, eczema, diabetic ulcers, bed sores, shingles, jock itch, athlete's foot, ringworm, and other dermal conditions. The composition also finds utility in preventing the development of nascent herpes outbreaks into herpes ulcers, in addition to providing long-lasting relief from such symptoms.

1 Claim, 2 Drawing Sheets

TOPICAL MEDICAMENT FOR TREATING SKIN ULCERS

BACKGROUND OF THE INVENTION

1. Field of the Invention

The instant invention relates generally to compositions for treating skin ulcers and particularly to compositions for medical or veterinary use containing sucralfate in combination with a topical anesthetic for treating skin ulcers.

2. Description of the Related Art

Compositions containing sucralfate or topical anesthetics are known in the art. For example, U.S. Pat. No. 5,246,697 (Conte, U., et al., Sep. 12, 1993) discloses the use of a sucralfate-containing gel as a vehicle for the application of drugs having topic activity.

U.S. Pat. No. 5,411,738 (Hind, H., May 2, 1995) discloses a composition and method for alleviating the pain associated with shingles utilizing the topical administration of lidocaine.

U.S. Pat. No. 5,478,814 (Packman, E. W., May 2, 1995) discloses a composition and method for treating hemorrhoids utilizing the topical administration of sucralfate in combination with a topically therapeutic agent, including an anesthetic.

U.S. Pat. No. 5,707,653 (Goldberg, A. H., Jan. 13, 1998) discloses a composition for treating internal or external ulcers which contains sucralfate in combination with an antibiotic.

SUMMARY OF THE INVENTION

The present invention is concerned with compositions for treating skin ulcers and particularly to compositions for medical or veterinary use containing sucralfate in combination with a topical anesthetic for treating skin ulcers.

A primary object of the present invention is to provide a composition and method for treating a wide variety of skin ulcers which utilizes a sucralfate in combination with lidocaine.

Another object of the present invention is to provide a composition and method for preventing the formation of herpes ulcers.

An additional object of the present invention is to provide a composition and method for promoting healing of diabetic ulcers.

Another object of the present invention is to provide a composition for treating skin ulcers which contains sucralfate in combination with a topical anesthetic and an antibiotic.

A further object of the present invention is to provide a composition for treating skin ulcers which provides both immediate relief from pain and long-lasting healing of the ulcer.

Another object of the present invention is to provide a composition for treating skin conditions such as acne, eczema, shingles, psoriasis, ringworm, jock itch, athlete's foot, burns and abrasions, which contains sucralfate in combination with one or more antibiotics, a topical anesthetic, or both.

Still another object of the invention is to provide a composition for treating sinus conditions containing sucralfate in combination with lidocaine.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DESCRIPTION OF THE PREFERRED EMBODIMENTS

Figure 1:
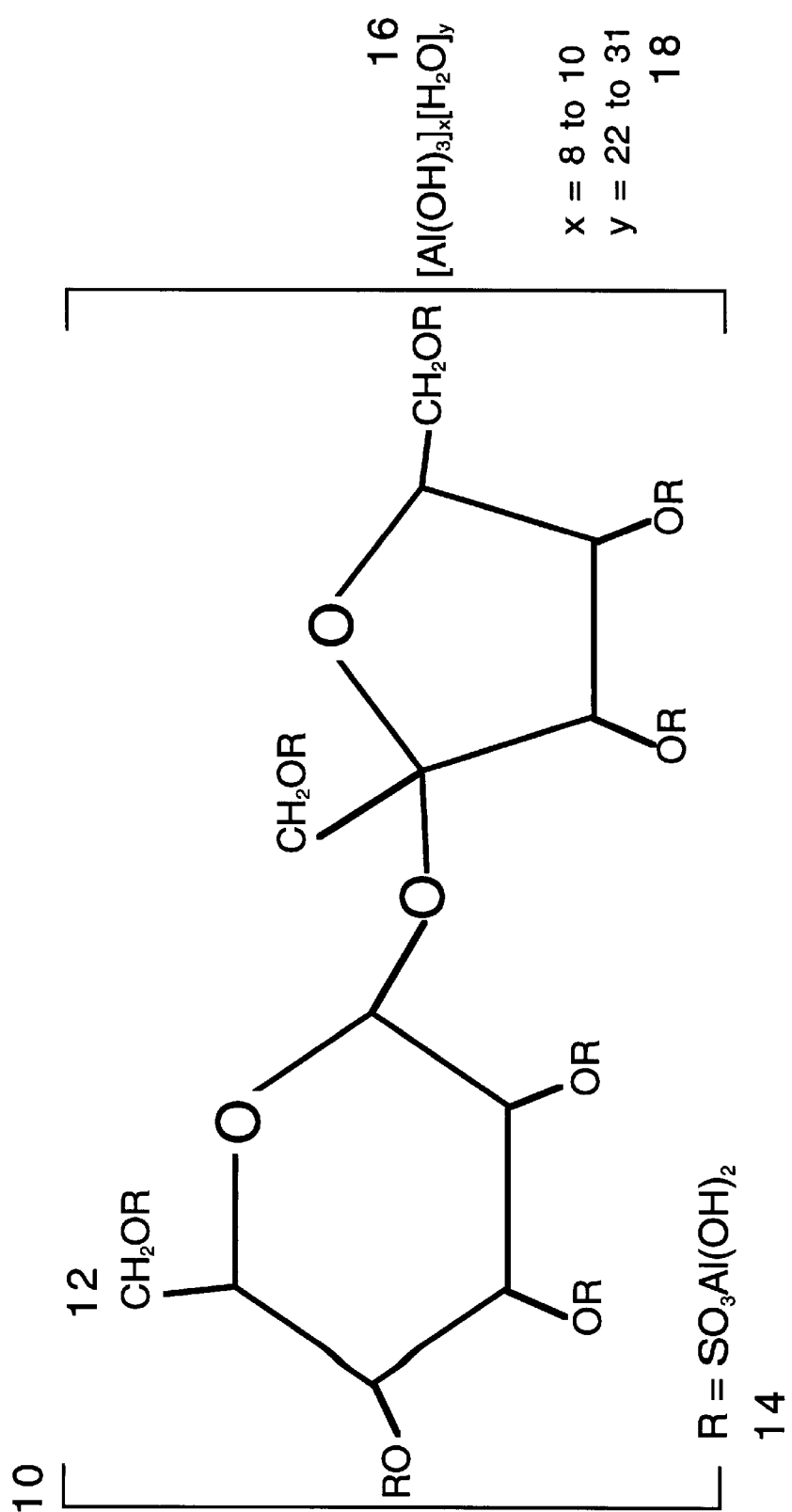
FIG. 1 illustrates the chemical structure for sucralfate.

Turning now descriptively to the drawings, in which similar reference characters denote similar elements throughout the several views, the Figures illustrate a composition for treating skin ulcers of the present invention. With regard to the reference numerals used, the following numbering is used throughout the various drawing figures.

10 chemical structure for sucralfate as an aluminum complex 12 non-complexed portion of 10

14 identification of R-groups of 12 as —$SO_3Al(OH)_2$ 16 aluminum complex portion of 10

18 definition of x and y from 16

Figure 2:
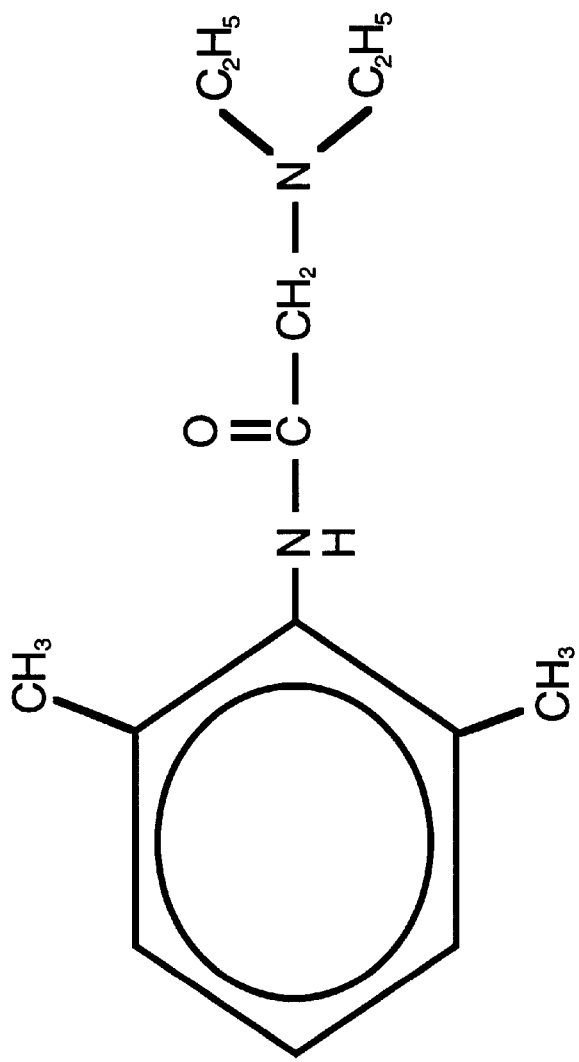
FIG. 2 illustrates the chemical structure for lidocaine.

20 chemical structure of lidocaine 22 chemical formula for lidocaine 24 molecular weight of lidocaine FIGS. 1 and 2 illustrate a composition for treating skin ulcers of the present invention. In its broadest embodiment, the present invention comprises a toppically-applicable composition including sucralfate 10 and a topical anesthetic or an antibiotic.

Sucralfate is an α-D-glucopyranoside, β-D-fructofuranosyl-, octakis-(hydrogen sulfate), aluminum complex as illustrated in FIG. 1. It is sold under the trade name CARAFATE®, in both tablet and liquid suspension form. It is most commonly dispensed for use in treating duodenal ulcers. The present invention is based on the finding that sucralfate, in combination with other active components such as topical anesthetics, antibiotics, antioxidants, vitamins and the like, can effectively treat a wide variety of topical conditions.

In preferred form, the composition of the invention includes sucralfate and lidocaine in combination. Lidocaine (Xylocaine®), is an amide originally synthesized from cocaine, and is one of the most widely used local anesthetics in use today. It is administered parenterally for ventricular arrhythmias, subcutaneously for minor surgical procedures, and topically to mucosal surfaces prior to invasive procedures. Available forms include a topical solution (2–4%), a rectal suppository (10%), an aerosol (10%), a jelly (2%), viscous lidocaine (2%), and a solution for intravenous and subcutaneous administration (0.5–2%).

The sucralfate is normally provided in suspension form, at a concentration of 1 g sucralfate per 10 ml of suspension. The preferred concentrations for the present invention results from the combination of 1 drop (about 0.1 g) of 2% lidocaine mixed together with about 0.25 fluid ounces (about 7.5 ml) of sucralfate suspension. When mixed in this proportion, the suspension thickens to the consistency of a gel, providing for ready administration to the patient.

Thus prepared, the composition of the present invention can be used to effectively treat a wide range of skin ailments, providing pain relief and promoting healing of any open ulcers. Additionally, further active components may be added to the composition as needed. For example, antibiotics and/or antifungal agents, vitamins such as vitamins A, C and E, plants extracts such as aloe vera or other plant materials which may promote healing, and combinations thereof.

Sucralfate binds preferentially to wound sites to form a protective coating thereon. Accordingly, the compositions of the present invention provide for the preferential delivery, to the wound site, of the various active components via the sucralfate in the composition. The effectiveness of the sucralfate in acting as a preferential carrier may be enhanced when the active component has an affinity for sucralfate, as many pharmaceutical products do. For example, the antibiotics tetracycline, doxycycline, nalidixic acid, the fluoroquinolone antibiotics ciprofloxacin, norfloxacin and ofloxacin, and the antifungal ketoconazole all have been shown to have some affinity for sucralfate and may find particular utility in the compositions of the present invention.

In addition to these compounds which adsorb to the sucralfate, other antibiotics also find utility in the compositions of the invention. This includes sulfa drugs and other antibiotics such as bacitracin, trimethoprim, penicillin and erythromycin. A preferred antibiotic is a combination of trimethoprim and sulfamethoxazole, in a weight ratio of 1:5, respectively, sold under the tradename Bactrim™.

The composition has been used to treat effectively many different ailments. For example, it has been used effectively to relieve pain and promote healing of diabetic ulcers, herpes ulcers, shingles, eczema, acne, psoriasis, skin rashes, burns and abrasions, and the like. In each instance, the patient reported immediate relief from the pain caused by the ulcers, and much more rapid healing of the wounds than when left untreated or treated by conventional methods. The composition has also been shown to be effective in treating sinus conditions where pain and inflammation are implicated.

The composition of the present invention has shown further, unexpected utility in preventing the development of herpes ulcers. It has been found that, when the composition of the present invention is applied to a nascent herpes outbreak (when a small bump occurs on the skin, the typical foreshadowing of an outbreak), the bump recedes within 1½ to 2 days, then disappears without developing into a herpes ulcer. Additionally, patients report that after so using the composition of the invention to stem the outbreak, the time between outbreaks is greatly extended, typically by a factor of 3 to 4. Therefore, the invention provides prophylactic utility for preventing herpes outbreaks. It is anticipated that such prophylactic utility extends also to other recurring conditions, such as psoriasis, diabetic ulcers, and the like.

The present invention can greatly alleviate the sympoms of chicken pox, and promotes the rapid healing of the associated skin eruptions such that scarring is avoided. The results are similar for treatment of infected skin rashes; pain relief was immediate and the skin appeared completely healed within 2 to 3 days.

In such conditions where antibiotics or antifungal agents are useful, the composition has also shown great efficacy. Such conditions include, for example, acne vulgaris, ringworm, jock itch, athlete's foot, conditions where infection is a concern, such as any open wounds, and the like.

It will be understood that each of the elements described above, or two or more together, may also find a useful application in other types of applications differing from the type described above. This includes, for example, veterinary applications as well as the medical applications described herein.

While the invention has been illustrated and described as embodied in a composition for treating skin ulcers, it is not intended to be limited to the details shown, since it will be understood that various omissions, modifications, substitutions and changes in the forms and details of the formulation illustrated and in its operation can be made by those skilled in the art without departing in any way from the spirit and scope of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims.

I claim:

1. A method of preventing a nascent herpes outbreak from developing into a herpes ulcer, comprising the topical administration of a composition as a prophylactic comprising sucralfate and lidocaine in a weight:weight ratio of from about 500:1 to about 200:1, respectively, and a pharmacentically effective amount of an antibiotic, in a pharmaceutically acceptable carrier to a site identified as a nascent herpes outbreak.

* * * * *